United States Patent
Bar-Ami et al.

[11] Patent Number: 6,129,214
[45] Date of Patent: Oct. 10, 2000

[54] SPERM STRAINER SYSTEM

[76] Inventors: Shalom Bar-Ami, 199 Pleasant St., Brookline, Mass. 02146; Amnon Weichselbaum, 2 Michael Street, Haifa, Israel, 34362

[21] Appl. No.: 09/216,286

[22] Filed: Dec. 18, 1998

Related U.S. Application Data

[60] Provisional application No. 60/068,240, Dec. 19, 1997.

[51] Int. Cl.[7] ........................ B07B 1/00
[52] U.S. Cl. .............. 209/235; 209/17; 209/248; 209/250; 209/255; 209/259
[58] Field of Search .............. 209/17, 235, 248, 209/249, 250, 255, 259

[56] References Cited

U.S. PATENT DOCUMENTS

| | | | |
|---|---|---|---|
| 4,007,087 | 2/1977 | Ericsson . | |
| 4,009,260 | 2/1977 | Ericsson . | |
| 4,439,319 | 3/1984 | Rock ........................... | 210/238 |
| 4,804,537 | 2/1989 | Bergman et al. ................ | 424/561 |
| 5,185,246 | 2/1993 | Deutsch . | |
| 5,427,946 | 6/1995 | Kricka et al. . | |
| 5,575,914 | 11/1996 | Jeyendran . | |
| 5,961,503 | 10/1999 | Simmet et al. ................ | 604/349 |

OTHER PUBLICATIONS

Research Instruments, Instruction Sheet No. 68B, Migration–Sedimentation Chamber, 1 page.

*Primary Examiner*—Donald P. Walsh
*Assistant Examiner*—Jonathan R Miller
*Attorney, Agent, or Firm*—Scott J. Asmus; Vernon C. Maine

[57] ABSTRACT

The invention in the simplest form is a passive method and apparatus for filtering motile sperm from a sperm sample. The invention passively filters the motile sperm using a nucleopore membrane that is contained within a membrane assembly, wherein the membrane assembly is disposed in a container. In operation, a medium is placed in the container so the membrane contacts the medium. A sperm sample is placed one side of the membrane assembly, and the motile sperm migrate through the membrane leaving the non-motile sperm behind, where they can be easily extracted.

16 Claims, 7 Drawing Sheets

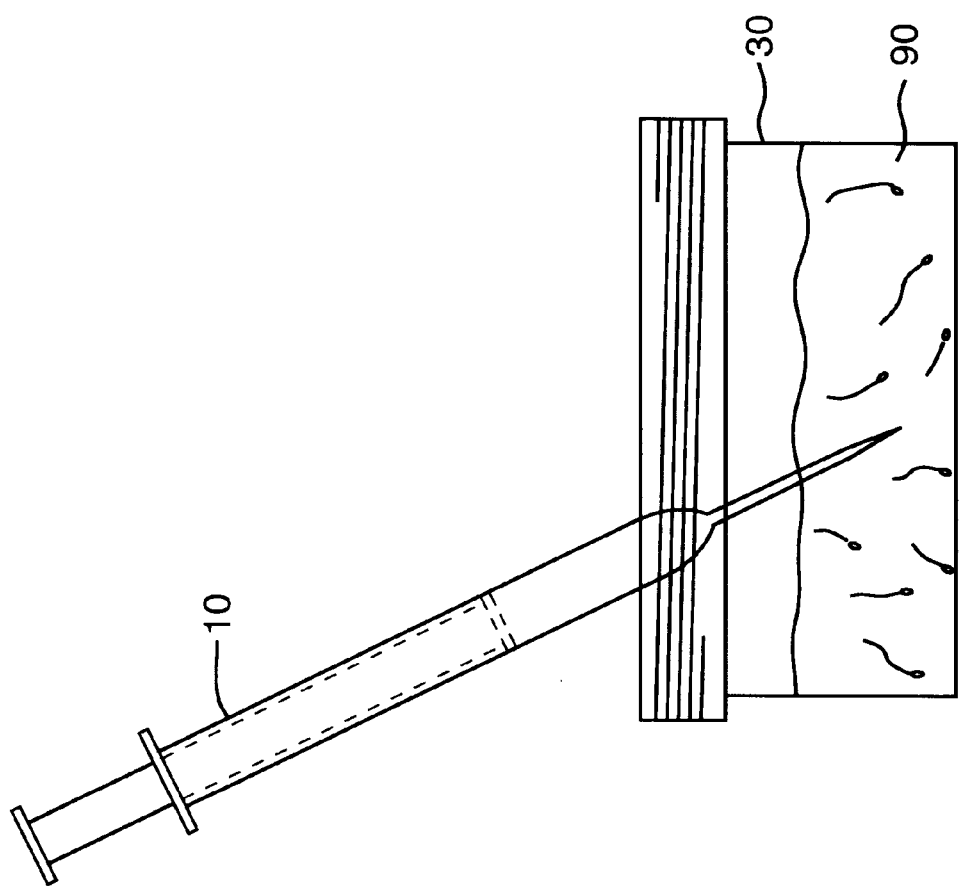

SPERM STRAINER SYSTEM

CROSS REFERENCE TO RELATED APPLICATIONS

This application claims priority under 35 U.S.C. §119(e) from a provisional patent Ser. No. 60/068,240 application filed on Dec. 19, 1997, which is incorporated herein by reference for all purposes.

BACKGROUND OF THE INVENTION

1. Field of the Invention

The present invention is a method and apparatus that provides an inexpensive, quick, and portable means to separate motile sperm from a sperm sample. The invention passively filters the motile sperm using a nucleopore membrane.

2. Background Art

Artificial insemination has become a much more frequent procedure due to a variety of sociological, economic, and perhaps environmental reasons. The number of inseminations in the United States and worldwide has been increasing, and will likely continue to increase in the next millennium. A number of causes have been cited for this increase. The age of childbearing has increased, as people are delaying children and marriage. The increased age lowers the probability of fertilization for both men and women. More and more women are also raising children by themselves without a partner, and electing artificial insemination as a means of fertilization. In addition, those that would otherwise not be able to have children now have a medical option that is relatively affordable. An additional factor may be that the sperm count among males has been declining, making fertilization more difficult. And finally, environmental factors have been blamed for decreased fertility of both men and woman.

There are currently a wide array of artificial insemination methods such as, intracervical, intrauterine (IUI), intratubular and direct intraperitoneal (DIPI) insemination, gamete intrafallopian transfer (GIFT), in vitro fertilization and embryo transfer (IVFET), zygote intrafallopian transfer (such as ZIFT, PROST and TET), peritoneal oocyte and sperm transfer (POST), and sex selection, among others. As technology advances, other methods are certain to follow, however, regardless of the process, high motile sperm are preferred.

As an example, the Intrauterine Insemination (IUI) and In Vitro fertilization (IVF) methods attempt to recreate the reproductive process by placing sperm and eggs together in an environment conducive to fertilization either in the womb or outside the womb. The fertilization process requires the sperm to actively invade the egg and commence fertilization. Motile sperm are much more likely to penetrate the egg.

A typical semen sample contains materials such as paternal plasma, protein, leukocytes, spermdecapitation factors and other extraneous materials, and dead, agglutinated or nonviable spermatozoa. These materials are known to interfere with successful fertilization, and with the successful maintenance of a fertilized ovum in the female patient. As an example, seminal plasma can cause severe uterine cramping, and in a worst case result in spontaneous abortion of the fertilized ovum. Thus, it is desirable to remove those spermatozoa having relatively low motility or possessing unhealthy, damaged or abnormal membranes.

The total number of sperm in an ejaculate is a measure of fertility, however, the percentage of motile sperm is much more important, especially when considering alternate reproductive means.

Sperm are categorized according to the their exhibited motility, as exhibited by Table 1, below.

TABLE 1

Motility Index

| Degree of Motility | Type of Motility |
|---|---|
| 0 | No motility, or movement of tail with no forward progression |
| 1 | 20% or less showing forward progression (sluggish movement) |
| 2 | 20%–50% showing forward progression |
| 3 | 50%–80% showing forward progression |
| 4 | 80%–100% showing forward progression (very rapid movement) |

The percentage or motile sperm showing progressive swimming movements is a measure of the fertility of the sperm sample. The higher the percentage, the higher quality of the sperm sample, and the greater the likelihood that the sample will achieve fertilization.

A high quality sperm sample is important for many reasons. The process of artificial insemination is not only costly economically, but is psychologically expensive. Unsuccessful attempts have devastating effects on the patients.

Higher quality sperm samples are also important considerations when the sample is subject to freezing or aqueous dilution, because these processes tend to kill or weaken the sample. Thus, only the highest quality sperm may survive the processing procedures to which the sperm are subjected.

In summary, higher viability spermatozoa are more likely to lead to successful fertilization and impregnation. The higher quality sperm are also more likely to survive freezing (cryopreservation) and other processing procedures.

In order to reduce the aforementioned problems, attempts have been made to provide a simple, portable, and inexpensive method and device for the filtration of sperm. However, the prior art devices and methods had significant disadvantages and shortcomings.

Various methods of selecting the more active sperm have been utilized in the past, such as the swim up. Swim down and Percoil density gradient centrifugation techniques. Swim-up methods are commonly used to process fresh or frozen specimens for the IUI and IVF procedures. The sperm is placed in a medium and subjected to a centrifuge process. The more motile sperm swim to a level where they can be extracted. Such methods employ multiple tube and centrifugation steps that are time consuming and can lead to a low recovery of motile sperm.

Table 2 below, provides a comparison of some features of these methods.

TABLE 2

Characteristics of Prior Art Methods

| Feature | Swim-Up | Strain Ex | Percoll | Enhance-S Plus |
|---|---|---|---|---|
| Sperm Preparation after liquefaction | None | None | 1 wash/centri- fugation | 1 wash/ centrifugation |

TABLE 2-continued

Characteristics of Prior Art Methods

| Feature | Swim-Up | Strain Ex | Percoll | Enhance-S Plus |
|---|---|---|---|---|
| Preparation of device | Prepare buffer solution, pour into plate | None | Build a 2 step gradient | Build a 2 step gradient |
| Sperm Quality | | | | |
| Motility | Higher % motile | Higher % motile | Same motility | Same motility |
| Viability | unknown | unknown | unknown | unknown |
| Leukocyte contaminants | unknown | unknown | unknown | unknown |
| Washes required after separation | None | None | 1–2 | 1–2 |
| Total # Centrifugation | 1 | 1 | 2–3 | 2–3 |
| Endotoxin Contamination | No | No | Yes | Yes |

One prior art device used for separating the motile sperm from a sperm sample is the migration-sedimentation chamber. This system uses a culture medium with the sperm sample suspended in the medium, and requires a centrifuge to rapidly spin the chamber to separate the motile sperm. And, because it is an active process, it increases the likelihood that motile sperm will be excluded from the sample set, or damaged during the process, thus producing a lower recovery sample.

In operation, the sperm sample is placed in a migration-sedimentation chamber, preferably in the lower well portion. The chamber is subjected to centrifugation, and the re-suspended sperm pellet is transferred to the gallery segment of the chamber. The portion of sperm in the well is the motile portion, and is used for insemination.

U.S. Pat. No. 5,185,246 ('246) is a method for semen analysis employing a membrane separation. This patent discloses a method to separate the particulate (cells, spermatozoa, and other particulate) in the whole semen from the seminal plasma which contains many soluble compounds, proteins, hormones, small molecules and electrolytes. The pore size is specifically designed for such a separation, and all sperm cells are blocked from passing through the membrane. The driving force of the '246 patent is a vacuum, and the sperm cells are stuck to the filter, dead and immobile, amenable only for in-situ testing or further disruption. A specific volume, preferably 100 microliters with various aqueous dilutions is employed. The separation apparatus of the '246 patent is a well filter plate that is used for multiple testing in the same round of processing.

The '246 patent is related to tests of andrological significance that need be performed on either the seminal plasma (in the absence of sperm cells) or on the surface of the sperm cells (in the absence of the seminal plasma). But, the cells in these cases need not be viable, need not be motile, and need not be freely dispersed in an aqueous buffered medium for retrieval. The '246 patent discloses a device for providing easier diagnostic access to specific components of the semen sample.

Another such invention is described in U.S. Pat. No. 5,575,914, which discloses a conduit that has glass wool as a strainer mechanism. The glass wool is compressed to a density sufficient to permit passage of the more motile sperm while blocking the lesser or non-motile sperm. In the preferred embodiment, the conduit is a nested pair of tubes that try to keep the glass wool density consistent.

The invention of U.S. Pat. No. 4,009,260 describes the fractionation of sperm through layered migration of different layers having differing densities. The more motile sperm penetrate deeper into the layers. Similarly, U.S. Pat. No. 4,007,087 also discloses the fractionation via layered solutions contacting the sperm sample.

U.S. Pat. No. 5,427,946 discloses a channeling apparatus, where there are inlet ports, flow channels, and nesting chambers. The sperm sample is applied at the inlet port, and only the motile sperm are capable of reaching the chambers.

In summary, problems heretofore exhibited in the art include having to purchase and maintain additional equipment such as a centrifuge. Prior methods required taking trips to other sites to perform the separation or centrifuge process. Other methods required extensive time to separate the motile sperm. In addition, prior art methods that used active separation schemes removed motile sperm and reduced the recovery lot.

What is needed is a method and apparatus that can passively isolate higher viability spermatozoa from the spermatozoa having relatively lower motility. The device should be inexpensive, portable, and easy-to-use. The method should be sufficient to screen out the lesser sperm and other compounds, leaving only high quality sperm for insemination. What is needed is an efficient device and method of removing the less motile sperm without costly or time-consuming procedures, and this new system should provide a quick and inexpensive way to increase the likelihood of fertilization.

SUMMARY OF THE INVENTION

The present invention has been made in consideration of the aforementioned background. It is therefore an object of the present invention to provide a system for conveniently, quickly, and inexpensively separating motile sperm from a sperm sample. This invention most generally relates to a method and an apparatus of straining sperm. In particular, it relates to a method of straining and separating motile sperm from a larger sample set without using additional machinery or devices.

One object of the present invention is to separate motile sperm from the non-motile sperm or leukocytes.

Another object o f the invention is to provide an inexpensive and easy to use device, such that each patient can use a clean sperm filter.

The membrane of the present invention is large enough to allow for the passage of sperm through the membrane. In the preferred embodiment, a 5–8 micron pore size is utilized.

The driving impetus of the present invention is the ability of quality sperm to move and swim through the membrane. The non-motile sperm and leukocytes move slightly, if at all, and therefore do not penetrate the membrane. No other force, such as a vacuum, suction, or gravity is required. Any artificially induced stress or pressure would defeat the purpose of the present invention by forcing non-motile sperm through the membrane and also possibly damaging the motile sperm by the applied force. The natural, self-actuated migration of the more motile sperm in the semen bath assures that the sperm that do encounter and work their way through the membrane will have a significantly higher average motility index than the remaining sperm.

The present invention further provides a method and apparatus for the separation of motile swimming cells from the dead/non-motile spermatozoa and from white blood cells that contaminate semen in case of inflammatory events. The present invention ascribes no significance to the separation of seminal plasma from the particulate matter since it is not a desired component that needs special care and attention.

The method and apparatus of the present invention is for the separation of the 'better' sperm, unattached to membranes or anything else, and in a form immediately available for retrieval and subsequent use in artificial insemination by means of a filtering membrane.

The motile sperm that penetrate the membrane may be supported in a buffered medium. After an incubation period, the motile sperm is immediately ready for functional analysis and the various methods of artificial insemination.

The cell strainer device in conjunction with the present methodology offers a rapid and efficient method for improving the sperm quality as a routine sperm preparation for artificial insemination. This sperm strainer device is a one-step system that enables the recovery of high-quality motile sperm in minimal time. No washing or centrifugation required, and the sperm preparation can be done in the office or at the desired location.

The preferred embodiment of the present invention includes a cell strainer unit with a 5 micron nylon mesh size and with an openable lid. This strainer is compatible with a 1 ml dish and has a screw cap. The 1 ml dish is used to hold the medium and retain the cell strainer unit when properly engaged. A disposable plastic pipette is used to place the sperm sample into the cell strainer, and a 1 ml disposable syringe with needle is used to place the medium into the dish and to extract the sperm sample when incubation is completed.

The method of operation of the preferred embodiment comprises placing 1 ml of a medium in the container or dish using the syringe with the needle. The user then puts 1–1.5 ml of liquefied semen into the strainer or membrane unit using a disposable plastic pipette. The lid on the strainer is closed, capturing the membrane or mesh securely in place, and the strainer unit is secured onto the dish. The unit is left for 30–45 minutes for incubation at 37° C. in 5% $CO_2$. At the end of the incubation period, the user can remove the strainer unit from the dish and discard the cell strainer. The sperm sample remaining in the dish is the motile sperm sample and the user can carefully aspirate all media from the dish, using the syringe with needle. The recovered sperm in media is ready to use for artificial insemination. For IUI applications, it is necessary to remove the needle from the syringe and attach the catheter and perform the IUI as normally done in the industry.

Tables 2, 3 and 4 below illustrate three actual examples of the original semen sample and the results of the Swim-Up Method of the prior art, as compared to the Cell-Strainer Method.

TABLE 2

Original versus Separation Results for Patient XY

| Patient XY | Original Semen | Swim-up Method | Cell-Strainer Method (Vertical) | Cell-Strainer Method (Horizontal) |
|---|---|---|---|---|
| Volume (ml) | 2.2 | 0.5 | 0.5 | 0.5 |
| Sperm count/ml (million) | 52 | 35 | 34 | 29 |
| Motility % | 55 | 72 | 70 | 73 |
| Progression | 3 | 4 | 4 | 4 |
| Velocity | 29 | 33 | 33 | 31 |
| Agglutination | None | None | None | None |
| Round Cells | 1.8 | 8.3 | 0.2 | 0.2 |

TABLE 3

Original versus Separation Results for Patient JM

| Patient JM | Original Semen | Swim-up Method | Cell-Strainer Method (Vertical) | Cell-Strainer Method (Horizontal) |
|---|---|---|---|---|
| Volume (ml) | 2.5 | 0.6 | 0.6 | 0.6 |
| Sperm count/ml (million) | 56 | 47 | 51 | 36 |
| Motility % | 61 | 71 | 77 | 75 |
| Progression | 3 | 4 | 4 | 4 |
| Velocity | 28 | 32 | 31 | 33 |
| Agglutination | None | None | None | None |
| Round Cells | 0.7 | 0.3 | 0.2 | 0.1 |

TABLE 4

Original versus Separation Results for Patient FJ

| Patient FJ | Original Semen | Swim-up Method | Cell-Strainer Method (Vertical) | Cell-Strainer Method (Horizontal) |
|---|---|---|---|---|
| Volume (ml) | 2.0 | 0.5 | 0.5 | 0.5 |
| Sperm count/ml (million) | 18 | 14 | 14 | 12 |
| Motility % | 68 | 85 | 87 | 89 |
| Progression | 3 | 4 | 4 | 4 |
| Velocity | 21 | 30 | 31 | 31 |
| Agglutination | None | None | None | None |
| Round Cells | 0.9 | 0.1 | 0.1 | 0.1 |

It will be readily apparent that all three methods result in reductions in total sperm count, however the total is still very high, viewed statistically, relative to the likelihood of achieving fertilization. More importantly, in ail cases the motility percentage is increased significantly. As is illustrated, in five out of six cases, the invention provided greater improvement in motility than the Swim-up method of the prior art.

The present invention is for a simple, inexpensive and disposable system for extracting motile sperm and preventing inferior sperm from entering the reproduction process. Artificial reproduction methods are costly and time-consuming procedures, and carry highly emotional overtones upon failure. It is important to increase the likelihood of successful reproduction, and the filtering of sperm is common in the industry. The prior methods of filtering out the motile sperm involved centrifuges and swim-up methods to extract the motile sperm. These methods are time-consuming and may lead to a low recovery of motile sperm, requiring additional equipment and steps in the fertilization process. The additional equipment and time lead to a higher overall cost.

Yet an additional object of the invention is to provide a membrane apparatus that completely encloses the sample sperm before placing the enclosed sample into the container medium. This 'tea bag' approach provides a maximum surface area for the motile sperm to disperse from the sample into the medium.

A further object is to provide a sperm strainer system that can be used for animals as well as humans. In the preferred embodiment, human sperm is considered, however the invention would work equally well with other sperm without deviating from the scope of the invention. With other types of sperm different sizes of mesh, and different mediums would be appropriate.

It is an object of the invention to provide a complete and portable sperm separation system. The invention can be packaged as a kit, and allow a fast and easy separation of the motile sperm. The kit would be not only cost effective, but can be used on locations that lack access to additional laboratory equipment required by the prior methods.

An additional object of the invention is to provide a sperm strainer apparatus for separating motile sperm from a sperm sample, where the sperm strainer apparatus comprises a container with a disposed medium, a membrane assembly, wherein the membrane assembly has a nucleopore membrane for passively separating the motile sperm from the sperm sample, and wherein the membrane assembly engages the disposed medium.

Yet a further object of the invention is to provide a sperm strainer apparatus having a lid attachable to the container.

An additional object of the invention is to provide a sperm strainer apparatus where the container has a threaded portion for engaging a mating threaded portion of the membrane assembly.

An object of the invention further includes a sperm strainer apparatus where the nucleopore membrane is 5–8 microns.

And a further object of the invention provides a sperm strainer apparatus wherein the nucleopore membrane is vertically disposed within the container.

Further object where a sperm fractionation apparatus having a membrane assembly that fits within the container and supports the nucleopore membrane at an angle relative to the bottom surface of the container and extending downward substantially to the bottom surface of the container.

An object where a sperm fractionation apparatus has a membrane assembly that fits within the container and rests on a plurality of stand-offs that create a gap between a bottom surface of the container and a bottom surface of the membrane assembly.

Further object, a method of separating motile sperm from a sperm sample comprising the steps of contacting the sperm sample to a first surface of a nucleopore membrane having pores of 5–8 microns in diameter through which motile sperm can generally migrate freely, contacting a receiving medium suitable for sustaining live sperm to the opposing surface of the nucleopore membrane, incubating the sperm sample and receiving medium in contact with the membrane at ambient pressure and absent application of centrifugal effects until a sufficient population of sperm have migrated to the receiving medium.

Additional object where a method o f separating motile sperm utilizing an apparatus comprising a container and a membrane assembly, the nucleopore membrane being supported by the membrane assembly, the container being configured to be divided into two chambers by the membrane assembly wherein the receiving medium can be contained in a first chamber in contact with the first surface of the nucleopore membrane and the sperm sample can be contained in a second chamber in contact with the second surface of the nucleopore membrane.

Further object a method of separating motile sperm, wherein the incubating is conducted for approximately 30 minutes.

Object where, a method of separating motile sperm, wherein the incubating is conducted at a temperature of approximately 37° C.

Object where a kit for the fractionation of motile sperm from a sperm sample by incubation at ambient pressure without application of centrifugal effects comprising, a container; a receiving medium; a membrane assembly configured with a nucleopore membrane having pores of 5–8 microns diameter, the container being divisible into two chambers by insertion of the membrane assembly wherein the receiving medium can be contained in a first chamber in contact with the first surface of the nucleopore membrane and the sperm sample can be contained in a second chamber in contact with the second surface of the nucleopore membrane, means for inserting and removing the receiving medium, and means for inserting and removing the sperm sample.

Object where a kit for the fractionation of motile sperm, further comprising a lid for covering the container.

Additional object where a kit for the fractionation of motile sperm, said means for inserting and removing saithed receiving medium comprising a syringe for displacing the medium.

And yet a further object includes kit for the fractionation of motile sperm the means for inserting and removing said sperm sample comprising a pipette Still other objects and advantages of the present invention will become readily apparent to those skilled in this art from the following detailed description, wherein I have shown and described only a preferred embodiment of the invention, simply by way of illustration of the best mode contemplated by me on carrying out my invention.

Other objects, features and advantages are apparent from the descriptions presented in conjunction with the accompanying drawings.

BRIEF DESCRIPTION OF THE FIGURES

FIG. 5 depicts a syringe removing the motile sperm from the container;

DESCRIPTION OF THE PREFERRED EMBODIMENT

To those skilled in the art, the invention admits of many variations. An enabling description of the preferred embodiment follows.

Figure 1:
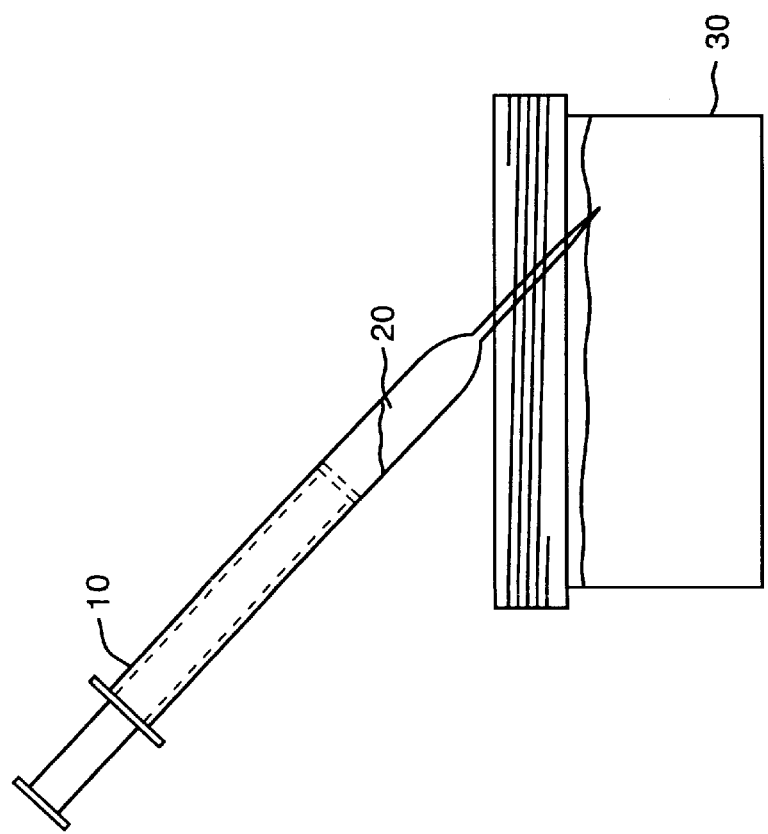
FIG. 1 shows the disposable syringe with a needle dispensing medium into a container.

Referring to FIG. 1, a 1 ml disposable syringe 10 is used to place approximately 1–1.5 ml of a desired medium 20 into a container or dish 30. There are various types of mediums commonly used in the industry, and the present invention would work with any of the mediums. The exact amount of medium is not important, although the rate of diffusion may be lower for lesser amounts. It is also possible to use the present invention with minimal target medium to obtain an undiluted sperm specimen.

The size and shape of the container can vary, although the smaller the container the more efficient and less costly the process. Plastic is the preferred construction material in order to reduce costs, but glass is also possible. In the preferred embodiment, the upper portion of the container or dish has a threaded outer surface for engaging and retaining the membrane assembly. However, it is within the scope of the invention to use other engaging and retaining methods such as inner threads, snaps, and press-fit closing devices.

Figure 2:
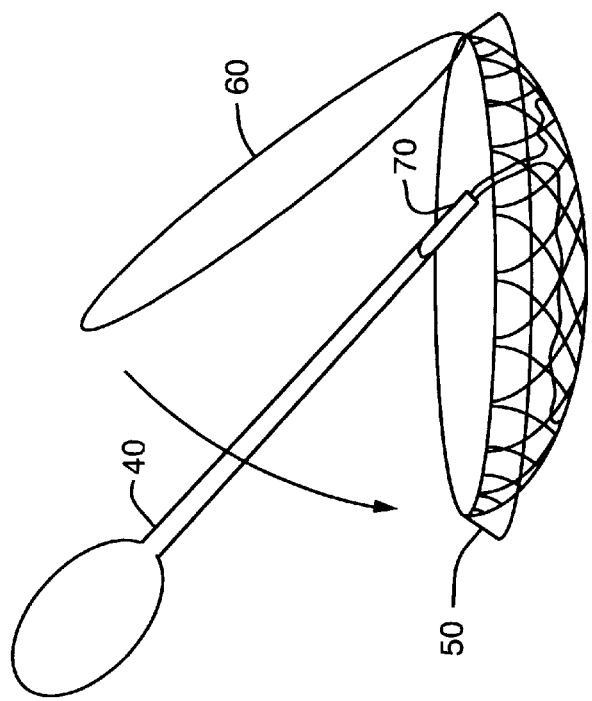
FIG. 2 shows the container and membrane assembly, and a plastic pipette placing the semen sample into the membrane assembly.

In FIG. 2, a disposable plastic pipette 40 is used to place the semen sample 70 into the sperm membrane assembly 50. in the preferred embodiment, 1–1.5 ml of sperm laden source or sample material 70 is placed into the unit. In practicing the invention, larger or smaller containers and corresponding membrane units or strainer devices may be utilized and still be within the scope of the invention. These other sizes allow for different amounts of sample and target medium, separating membrane surface area, and sperm, in order to maximize the transfer of the motile sperm for the particular purpose and the medium used.

In the preferred embodiment, the unit has a lid attachment 60 that closes onto the mesh membrane. It prevents the mesh from falling into the dish 30, aids in maintaining the correct temperature, and prevents particles from falling into the strainer unit. The lid is not a requirement relative to the functioning of the mesh for separation, and other methods can be used to retain the mesh on the strainer without using the lid.

The nylon mesh in the preferred embodiment has a pore size of 5–8 microns, although variations are within the scope of the invention. A finer pore size would further restrict the sperm and yield even a higher quality sperm but reduce the sample size. A greater pore size would allow more sperm to pass into the dish, but introduce less motile sperm. Non-human sperm samples may require different pore sizes. Nylon mesh is used for membrane of the present invention, although the invention works equally well with other mesh materials.

Figure 3:
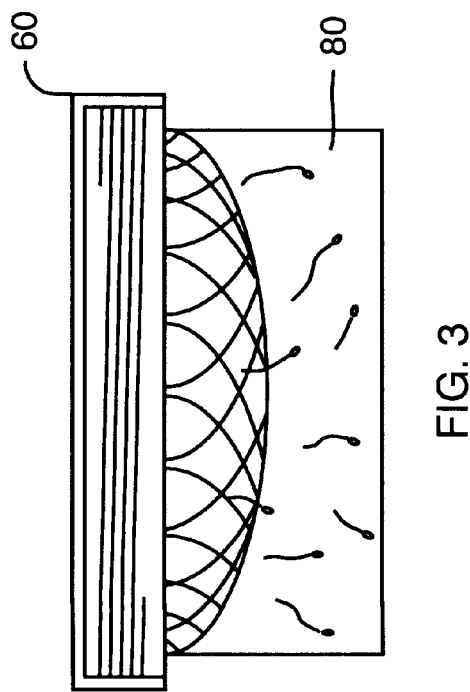
FIG. 3 is an illustration of the incubation process.

FIG. 3 depicts the incubation process, wherein the motile sperm 80 migrate through the mesh barrier and enter into the target section. As shown, the cell strainer unit with the lid 60 closed is screwed onto the dish, and the sperm swim or migrate about in the sample or source section until they encounter and penetrate the mesh barrier membrane into the target medium.

In the preferred embodiment, the incubation process lasts thirty minutes at 37° C., although it depends on many variables. The amount of the medium, the surface area and pore size of the mesh, the temperature, the amount and density of sperm in the medium, and the mobility of the sperm are all factors that should be considered in determining the incubation period.

Figure 4:
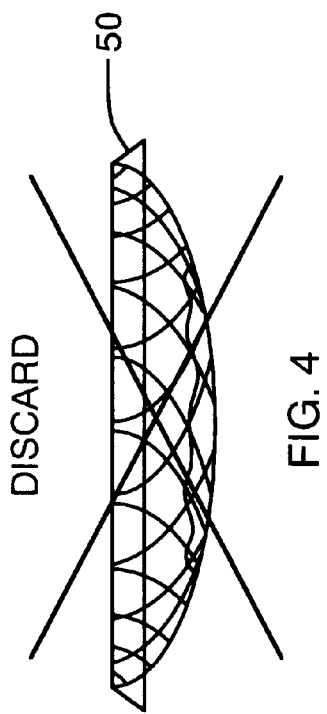
FIG. 4 illustrates the ease and convenience of the clean-up process by discarding the cell strainer unit.

At the end of the incubation period, the membrane apparatus 50 is removed from the dish with the remaining portion of the original sample, as shown in FIG. 4. The membrane apparatus 50 with the remaining original sample can be closed with the lid and disposed of appropriately. The membrane apparatus can be easily discarded as shown in FIG. 4, eliminating messy clean-up.

As shown in FIG. 5, the target medium 90 now contains the recovered sperm, ready for fertilization purposes. The dish with the threaded portion containing the refined sperm specimen can be closed with a lid and conveniently transported, or the specimen can easily be extracted using a syringe and immediately used.

Figure 6C:
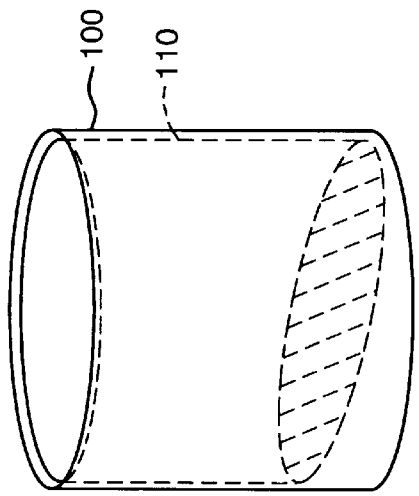
FIG. 6(c) shows the membrane assembly placed in the container.
Figure 6B:
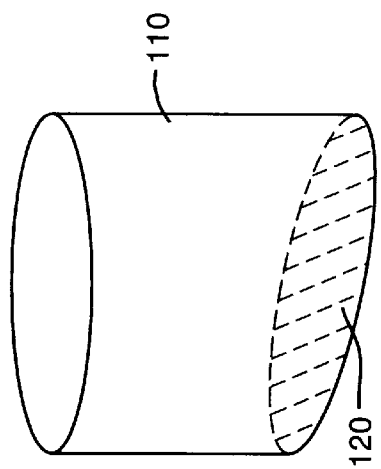
FIG. 6(b) shows a membrane assembly.
Figure 6A:
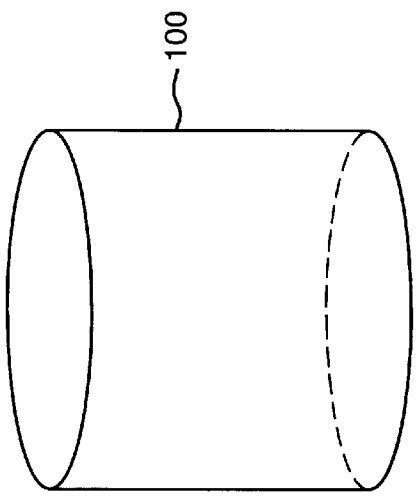
FIG. 6(a) shows a container.

FIGS. 6(a), (b), and (c) illustrate an alternate embodiment of the invention. An outer cell 100 is preferably made of plastic and conical in design. An inner cell 110 is also made of plastic, and conical in design. The inner cell 110 has a slightly smaller radius than the outer cell 100, so that the inner cell 110 can fit within the outer cell 100. The bottom surface of the inner cell 110 has a nucleopore membrane 120 with a pore size of between 5–8 microns. This is the optimal pore size that allows human motile sperm to penetrate, while leaving the dead or less motile sperm behind. Other pore sizes are within the scope of the invention to accommodate other sperm sizes as for animals other than humans.

In this embodiment, the bottom surface membrane of the inner cell is elliptical in shape to provide greater surface area, and arranged at an angle that divides the volume in the lower region of the outer cell diagonally into a source volume and a target volume.

In operation, a suitable receiving medium is placed in the target volume area, as shown in FIGS. 6(a) and (b). The inner cell 110 is placed inside the outer cell 100 such the lower end of the slanted bottom surface membrane extends substantially down to the inner bottom surface of the outer cell, and that ail or substantially all of the bottom surface membrane is wetted by the receiving medium. The sperm sample is placed in the inner cell on the nucleopore membrane and should cover substantially all of the membrane to assure the largest transfer surface area between the two mediums. A lid 130 is placed onto the cells and the system is allowed to incubate for about thirty minutes at approximately 37° C.

Figure 7C:
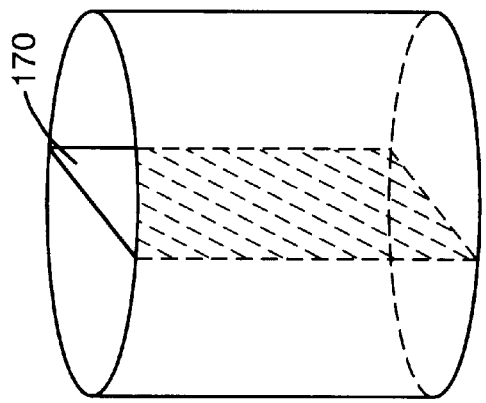
FIG. 7(c) shows the vertical membrane assembly placed in the container.
Figure 7B:
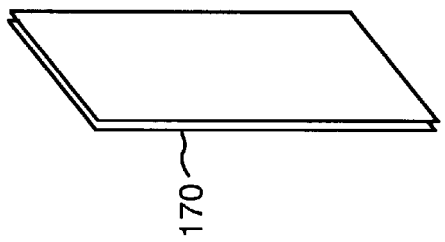
FIG. 7(b) shows an exploded view of the vertical membrane assembly.
Figure 7A:
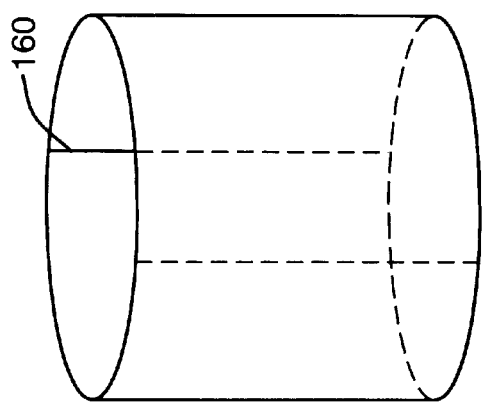
FIG. 7(a) shows a container with a track member.

Another embodiment uses a conical container that has a grooved inner surface 160 that divides the interior volume vertically into two halves, as shown in FIGS. 7(a), (b), and (c). A framed membrane section 170 that has a 5–8 micron nucleopore membrane is inserted into groove 160 of the container. This mating groove helps retain a tight fit against the inner wall of the container. The groove is not a necessary component, as the framed section can be placed into a container having no groove, as long as the fit assures there will be no leakage. The framed member section 170 can have rubber, elastic, or other soft outer perimeter to retain a tight fit on the inside wall of the container. A lid 200 with a lower side groove can also aid in keeping the framed membrane in place.

In operation as shown in FIG. 7(c), the vertical separation scheme is illustrated. The framed membrane creates two compartments in the container, a sample side and a receiving side. A buffer medium is added to the receiving side, and a sperm sample is introduced into the sample side. The stronger motile sperm migrate through the nucleopore membrane in the manner of the invention, populating the receiving side with a relatively high motility sperm set.

Figure 8C:
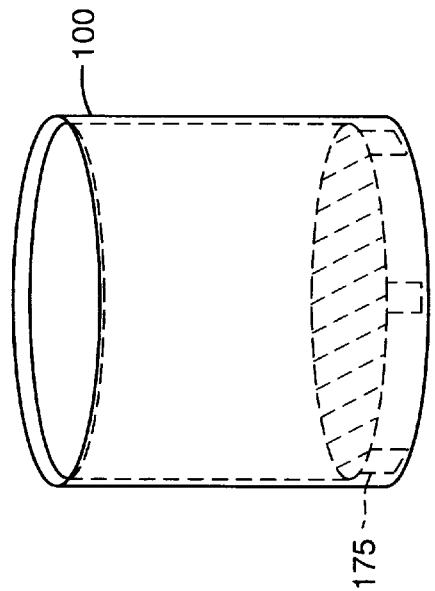
FIG. 8(c) shows the membrane assembly placed in the container.
Figure 8B:
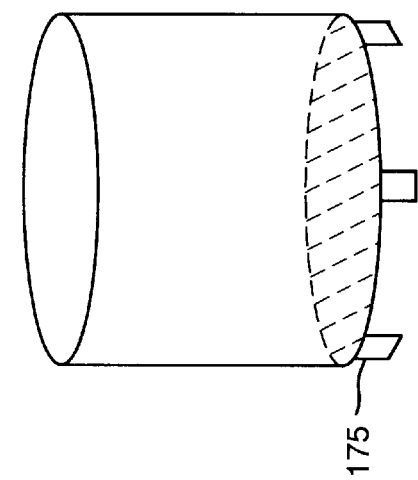
FIG. 8(b) shows a membrane assembly with standoffs.
Figure 8A:
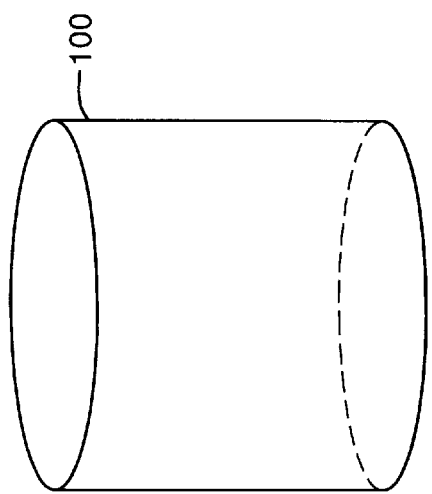
FIG. 8(a) shows a container.

FIGS. 8(a), (b), and (c) illustrate a further variation, where the inner container has standoffs 175 on the bottom surface. The standoffs keep the inner container a small distance from the bottom surface of the outside container to allow the sperm to settle and accumulate in this region. The standoffs can be on the inner container or the outer container, as long as it keeps the bottom surface of the inner container a small distance from the bottom surface of the outer container.

Figure 9B:
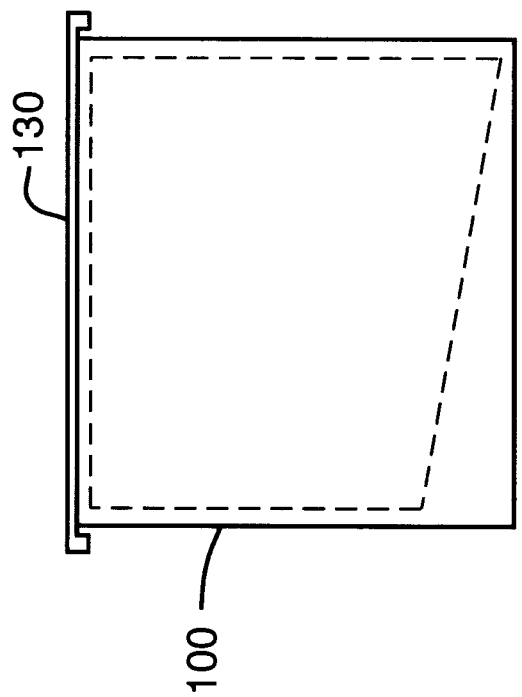
FIG 9(b) shows a side view of the container and membrane assembly with a lid.
Figure 9A:
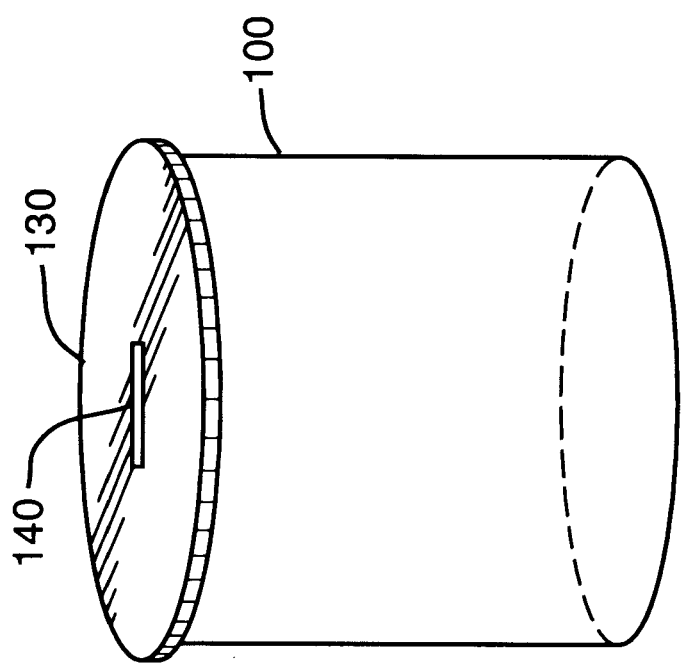
FIG. 9(a) shows a container with a lid.

The lid 130 is made to cover the inner and outer cells and prevent foreign debris from entering the cells, as shown in FIGS. 9(a) and (b). The lid 130 can be designed with a small slit 140 to provide ventilation and allow the cover to be removed with simple instruments. A handle can also be installed to allow easy access. The outer perimeter of the lid can envelop the outer circumference of the outer container 100, or be retained within the outer or inner containers and rest on the top surface of the container. A notched perimeter allows for better seating of the lid and is within the scope of the invention.

As will be realized, the invention is capable of other and different embodiments and its several details are capable of modifications in various obvious respects, all without departing from the invention.

In summary, the invention is distinguished from the prior art by providing a passive separation of the motile sperm in a disposable and convenient system. The system is cost effective as compared to existing methods and allows on-site preparation of motile sperm for fertilization. It is less time consuming than other processes, and does not require extra equipment or taking the sample to a separate lab.

The foregoing description of the preferred embodiment of the invention has been presented for the purpose of illustration and description. It is not intended to be exhaustive or to limit the invention to the precise form disclosed. Many modifications and variations are possible in light of the above teachings. It is intended that the scope of the invention be limited not by this detailed description, but rather by the claims appended hereto.

The invention is susceptible of many variations, all within the scope of the claims. The preferred embodiment described here and illustrated in the figures should not be construed as in any way limiting.

No warranty is expressed or implied as to the actual degree of safety, security or support of any particular specimen of the invention in whole or in part, due to differences in actual production designs, materials and use of the products of the invention.

We claim:

1. A sperm fractionation apparatus for separating motile sperm from a sperm sample comprising:
    a nucleopore membrane with first and second opposing surfaces through which motile sperm can generally migrate freely;
    a receiving medium suitable for sustaining live sperm; and
    a means for contacting said receiving medium with said first surface of said membrane and said sperm sample with said second surface of said membrane, thereby creating a transfer path through which migrating motile sperm can pass from said sample to said receiving medium.

2. The sperm fractionation apparatus of claim 1, said means for contacting comprising a container and a membrane assembly, said nucleopore membrane being supported by said membrane assembly, said container being configured to be divided into two chambers by said membrane assembly wherein said receiving medium can be contained in a first chamber in contact with said first surface of said nucleopore membrane and said sperm sample can be contained in a second chamber in contact with said second surface of said nucleopore membrane.

3. The sperm fractionation apparatus according to claim 2, further comprising a lid attachable to said container.

4. The sperm fractionation apparatus according to claim 2, wherein the container has a threaded portion for engaging a mating threaded portion of said membrane assembly.

5. A sperm fractionation apparatus according to claim 1, wherein the pores of said nucleopore membrane are 5–8 microns in diameter.

6. A sperm fractionation apparatus according to claim 2, wherein said nucleopore membrane is vertically disposed within said container.

7. A sperm fractionation apparatus according to claim 2, wherein said membrane assembly fits within said container and supports said nucleopore membrane at an angle relative to said bottom surface of said container and extending downward substantially to said bottom surface of said container.

8. A sperm fractionation apparatus according to claim 2, wherein said membrane assembly fits within said container and rests on a plurality of stand-offs that create a gap between a bottom surface of said container and a bottom surface of said membrane assembly.

9. A method of separating motile sperm from a sperm sample comprising the steps:
    contacting said sperm sample to a first surface of a nucleopore membrane having pores of 5–8 microns in diameter through which motile sperm can generally migrate freely,
    contacting a receiving medium suitable for sustaining live sperm to the opposing surface of said nucleopore membrane,
    incubating said sperm sample and receiving medium in contact with said membrane at ambient pressure and absent application of centrifugal effects until a sufficient population of sperm have migrated to said receiving medium.

10. A method of separating motile sperm according to claim 9, said method utilizing an apparatus comprising a container and a membrane assembly, said nucleopore membrane being supported by said membrane assembly, said container being configured to be divided into two chambers by said membrane assembly wherein said receiving medium can be contained in a first chamber in contact with said first surface of said nucleopore membrane and said sperm sample can be contained in a second chamber in contact with said second surface of said nucleopore membrane.

11. A method of separating motile sperm according to claim 10, wherein said incubating is conducted for approximately 30 minutes.

12. A method of separating motile sperm according to claim 10, wherein said incubating is conducted at a temperature of approximately 37° C.

13. A kit for the fractionation of motile sperm from a sperm sample by incubation at ambient pressure without application of centrifugal effects comprising:
    a container;
    a receiving medium;
    a membrane assembly configured with a nucleopore membrane having pores of 5–8 microns diameter, said container being divisible into two chambers by insertion of said membrane assembly wherein said receiving medium can be contained in a first chamber in contact with said first surface of said nucleopore membrane and said sperm sample can be contained in a second chamber in contact with said second surface of said nucleopore membrane,
    means for inserting and removing said receiving medium, and
    means for inserting and removing said sperm sample.

14. A kit for the fractionation of motile sperm according to claim 13, further comprising a lid for covering said container.

15. A kit for the fractionation of motile sperm according to claim 13, said means for inserting and removing said receiving medium comprising a syringe for displacing said medium.

16. A kit for the fractionation of motile sperm according to claim 13, said means for inserting and removing said sperm sample comprising a pipette.

* * * * *